United States Patent
Lang et al.

(12) 
(10) Patent No.: US 6,468,505 B1
(45) Date of Patent: Oct. 22, 2002

(54) TECHNIQUE TO MONITOR DRUG DELIVERY NONINVASIVELY IN VIVO

(75) Inventors: Philipp Lang, San Francisco, CA (US); Olivier Meyer, Strasbourg (FR); Michael F. Wendland, Benicia, CA (US); Maythem Saeed, Novato, CA (US)

(73) Assignee: Philipp Lang, Lexington, MA (US)

(*) Notice: Subject to any disclaimer, the term of this patent is extended or adjusted under 35 U.S.C. 154(b) by 0 days.

(21) Appl. No.: 09/696,352

(22) Filed: Oct. 24, 2000

Related U.S. Application Data

(63) Continuation of application No. 09/413,088, filed on Oct. 6, 1999, now abandoned, which is a continuation of application No. PCT/US98/07012, filed on Apr. 8, 1998.
(60) Provisional application No. 60/043,868, filed on Apr. 9, 1997.

(51) Int. Cl.[7] .......................... A61B 5/055; A61K 9/127
(52) U.S. Cl. ..................... 424/9.321; 424/450
(58) Field of Search .............................. 424/9.321, 9.3, 424/9.36, 450

(56) References Cited

U.S. PATENT DOCUMENTS

| | | |
|---|---|---|
| 3,932,657 A | 1/1976 | Rahman |
| 4,590,060 A | 5/1986 | Ehrenfeld |
| 4,728,575 A | 3/1988 | Gamble et al. |
| 4,985,233 A | 1/1991 | Klaveness et al. |
| 5,013,556 A | 5/1991 | Woodle et al. |
| 5,019,369 A | 5/1991 | Presant et al. |
| 5,213,788 A | 5/1993 | Ranney |
| 5,213,804 A | 5/1993 | Martin et al. |
| 5,215,680 A | 6/1993 | D'Arrigo |
| 5,312,617 A | 5/1994 | Unger et al. |
| 5,387,410 A | 2/1995 | Bosworth et al. |
| 5,393,530 A | 2/1995 | Schnieder et al. |
| 5,407,660 A | 4/1995 | Bosworth et al. |
| 5,512,294 A | 4/1996 | Li et al. |
| 5,527,528 A | 6/1996 | Allen et al. |
| 5,545,395 A | 8/1996 | Tournier et al. |
| 5,582,172 A | 12/1996 | Papisov et al. |
| 5,593,688 A | 1/1997 | Baldeschwieler |
| 5,620,703 A | 4/1997 | Reszka et al. |
| 5,705,187 A | 1/1998 | Unger |
| 5,780,010 A * | 7/1998 | Lanza et al. ............... 424/9.32 |
| 5,820,873 A * | 10/1998 | Choi et al. ............... 424/283.1 |
| 6,132,763 A * | 10/2000 | Fisher et al. ............... 424/450 |

FOREIGN PATENT DOCUMENTS

| | | |
|---|---|---|
| DE | 4341478 | 6/1995 |
| WO | WO 98/44910 | 10/1998 |

OTHER PUBLICATIONS

Brasch, (1991) Magn. Res. Med. 22:282–287.
Gaber, (1995) Pharmaceutical Research 12:1407–1416.
Harding, (1997) Biochim. Biophys. Acta. 1327(2):181–192.
Huang, (1994) Cancer Research 54:2186–2191.
Kirpotin, (1997) Biochemistry 36(1):66–75.
Lasic and Papahadjopoulos, (1995) Science 267:1275–1276.
Oksendal and Hals, (1993) JMRI 3:157–165.
Olson, (1979) Biochimca. et. Biophysica. Acta. 557:9–23.
Park et al., Cancer Letters 118(2):153–160, 1997.
Papahadjopoulos & Gabizon, in Liposomes as Tools in Basic Research & Industry, 177–184 (Philippot, J.R. & Schuber, F. eds.) (1994).
Rocklage and Watson, (1993) JMRI 3:167–178.
Seltzer et al., (1995) Radiology 194:775–781.
Tilcock et al., (1989) Radiology 171:77–80.
Tilcock et al., (1992) Biochim. Biophys. Acta 110:193–198.
Tilcock, in Liposomes as Tools in Basic Research & Industry, 225–236 (Philippot, J.R. & Schuber, F. eds., 1994).
Trubetskoy et al., (1995) Magn. Res. Imaging 13:31–37.
Unger et al., (1989) Radiology 171:81–85.
Unger et al., (1988) Invest. Radiol. 23:928–932.
Witzel and Prescher, (1991) Invasion Metastatis 11:110–115.
Woodle, (1993) Nucl. Med. Biol. 20:149–155.

* cited by examiner

*Primary Examiner*—Michael G. Hartley
(74) *Attorney, Agent, or Firm*—Swanson & Bratschun, LLC

(57) ABSTRACT

The present invention relates to the field of diagnostic imaging and more specifically to the field of monitoring drug delivery using non-invasive imaging techniques. The present invention provides for imaging agents and compositions useful for NMR, computed tomography, scintigraphy, PET and any other type of imaging where the imaging agent can be carried by liposomes or other lipid based vehicles, such as micelles or suspended lipid aggregates.

21 Claims, 2 Drawing Sheets

TECHNIQUE TO MONITOR DRUG DELIVERY NONINVASIVELY IN VIVO

CROSS REFERENCE TO RELATED APPLICATIONS

This application claims the benefit of all rights accorded under Sections 120 with respect to the following applications and is a continuation of U.S. application Ser. No. 09/413,088, filed on Oct. 6, 1999 now abandoned, by Lang, Meyer, Wendland and Saeed, now abandoned, which is a continuation of PCT application Ser. No. PCT/US98/07012, filed Apr. 8, 1998, published as International publication number, WO 98/44910 and which claims priority under 35 U.S.C. §119 from U.S. provisional application serial No. 60/043,868, filed on Apr. 9, 1997, by Lang, Meyer, Wendland and Saeed, which are all incorporated herein by reference.

TECHNICAL FIELD

The present invention relates to the field of diagnostic imaging and more specifically to the field of monitoring drug delivery using non-invasive imaging techniques.

INTRODUCTION

Multiple contrast agents are available for enhancing tissue contrast in magnetic resonance Imaging. Some of the most commonly used contrast agents are chelates of Gadolinium, such as Gd-DTPA, Gd-DTPA-BMA, and Gd-DOTA. Most currently available contrast agent formulations are of small molecular size. In imaging the brain, small molecular contrast agents will not cross the normal, intact blood brain barrier. Contrast enhancement is only seen in pathologic regions with disturbance or disruption of the blood brain barrier.

In imaging the body, however, no barrier with functions similar to those of the blood-brain-barrier exists except for the ovary and testicles. All clinically available small molecular agents will cross the endothelial membrane easily and will be rapidly excreted by the kidney. Thus, with small molecular contrast agents, enhancement will be observed with both pathologic, as well as normal, tissue. Macromolecules of sufficient size, however, will not permeate normal endothelium unless they are taken up by the reticuloendothelial system. Only when capillary permeability is increased, as it is the case with tumors, can such macromolecules extravasate through the endothelial membrane and accumulate in the tissue, e.g. tumor tissue.

Several prototype macromolecular MR contrast agents agents have been developed such as Gd-DTPA bound to albumin (see Brasch "Rationale and applications for macromolecular Gd-based contrast agents" Magn Res Med, 22, 282–287, (1991)), Gd-DTPA bound to carbohydrates (see Klaveness, et al. "A diagnostic agent containing a non-radioactive paramagnetic metal species in a macromolecular carrier" United States Patent, (1991)), and Gd-chelates bound to polylysine. While all of these agents hold the potential to be used as macromolecular contrast agents in-vivo in human subjects, they are hampered by multiple problems. Albumin-Gd-DTPA, for example, suffers from significant antigenicity (see Brasch "Rationale and applications for macromolecular Gd-based contrast agents" Magn Res Med, 22, 282–287, (1991)) and anaphylactic reaction may occur after injection. Inadequate size is another problem. If the compound is too large, it will not extravasate through the endothelial membrane. If the compound is too small, it may again permeate into normal rather than pathologic tissues only. Finally, renal or hepatic excretion of the macromolecular compounds is often Insufficient for clinical use (see Brasch "Rationale and applications for macromolecular Gd-based contrast agents" Magn Res Med, 22, 282–287, (1991)).

The present invention provides for imaging agents that selectively target pathologic or cancerous tissues compared with normal or non-cancerous tissues with use of liposomes with prolonged circulation time and discloses the use of such formulations for monitoring delivery of therapeutic agents or drugs to a lesion such as a tumor.

SUMMARY

The present invention provides for imaging agents and compositions useful for NMR, scintigraphy, PET and any other type of imaging where the imaging agent can be carried by liposomes. Generally, the imaging composition comprises an imaging agent, with a liposome with an agent that increases blood circulation life time and a therapeutic agent that is selected for a particular type of treatment or tissue, such as cancer or tissues with increased capillary permeability. For instance, the invention provides for a composition for NMR imaging during drug delivery, comprising:

a) a paramagnetic chelate with a paramagnetic ion and in amount sufficient to enhance NMR imaging, b) a liposome comprising a bilayer and an interior volume, wherein said liposome is in an amount sufficient to permit selective delivery of said liposome to a tissue compared to delivery in the absence of said liposome, and said liposome carries said paramagnetic chelate, c) a polyalkylether associated with said liposome, and d) a therapeutic agent in an therapeutic amount, wherein said liposome carries said therapeutic agent.

PREFERRED EMBODIMENTS

Figure 1:
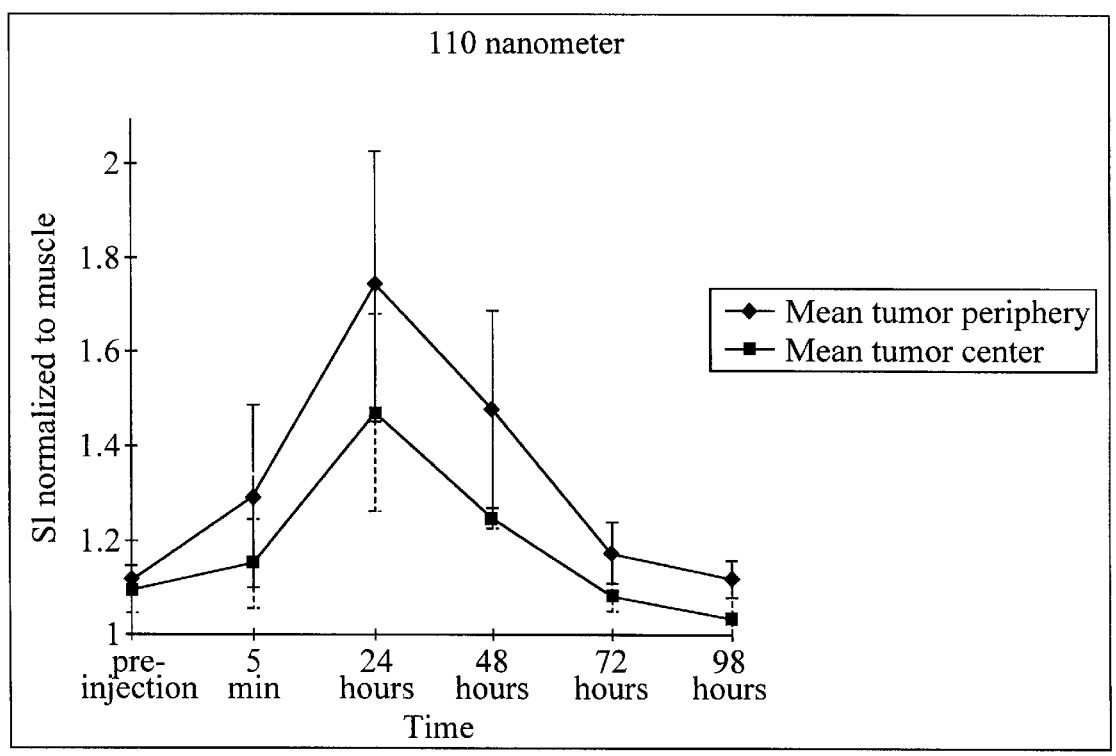
FIG. 1 is graphic presentation of normalized mean signal intensity of tumor periphery and tumor center measured at various time intervals before and after injection of 110 nm diameter liposomes containing Gd-DTPA-BMA. Error bars indicate one standard deviation.
Figure 2:
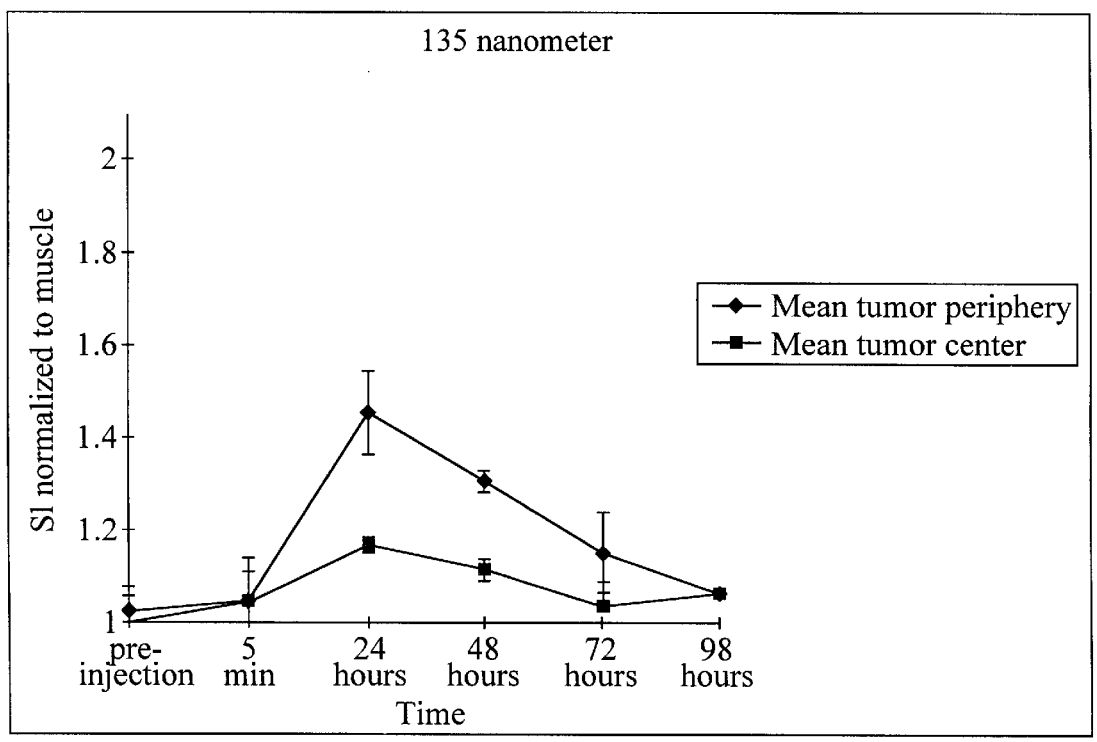
FIG. 2 is graphic presentation of normalized mean signal intensity of tumor periphery and tumor center measured at various time intervals before and after injection of 135 nm diameter liposomes containing Gd-DTPA-BMA. Error bars indicate one standard deviation.

The present invention provides for imaging agents and compositions useful for NMR, computed tomography, scintigraphy, PET and any other type of imaging where the imaging agent can be carried by liposomes or other lipid based vehicles, such as micelles or suspended lipid aggregates. Such imaging agents are known in the art, for example see *Magnetic Resonance Imaging of the Body,* Editor C. Higgins et al., especially Chapters 50–55. Generally, the imaging composition comprises an imaging agent, with a liposome with an agent that increases blood circulation life time (e.g. polyalkylether modification) and a therapeutic agent that is selected for a particular type of treatment or tissue, such as cancer or tissues with increased capillary permeability. For instance, the invention provides for a composition for NMR imaging during drug delivery, comprising:

a) a paramagnetic chelate with a paramagnetic ion and in amount sufficient to enhance NMR imaging,
b) a liposome comprising a bilayer and an interior volume and in an amount sufficient to permit selective delivery of said liposome to a tissue compared to delivery in the absence of said liposome, wherein said liposome carries said paramagnetic chelate,
c) a polyalkylether associated with said liposome, and
d) a therapeutic agent in an therapeutic amount, wherein liposome carries said therapeutic agent.

A variety of paramagnetic chelates can be used, such as BOTPA, EHPG, DPDP, DTPA, DOA3 and HBED or any other NMR imaging agent known in the art or developed in the future. Typically, the polyalkylether is poly (ethyleneglycol) and other means of increasing liposome half life in the blood can be used as known in the art. The preferred liposome has an average size distribution of about 85 nanometers in diameter, although about 50 to 190 nanometer diameters lipid vehicles can be used. Size selection can be made using any sizing method, including filtration or Coulter counting. Typically, lipids used to make the liposomes will be selected to provide increased blood half life and of sufficient permeability to act as good carriers of agents while permitting imaging. Such liposomes can comprise a molecule selected form the group consisting of phosphatidyl ethanolamine, phosphatidyl choline, dipalmitoyl phosphatidic acid, cholesterol and alpha-tocopherol. If poly(ethylene glycol) is used, it is preferably present in the amount of between about 5 to 10 mole percent of total lipid content. The liposomes usually have an interior volume with a pH of 5.5 to 7.5 and are isotonic to the blood. Preferably, the liposomes will target a solid tumor in a non-reticuloendothelial organ or a solid tumor in liver or spleen. Usually, the liposomes will alter the T1 relaxation time of an NMR imaging agent (contrast agent carried by liposomes versus free contrast agent) by at least 5%, preferably by at least 10%, more preferably by at least 20% and most preferably by 30–80%. Preferably, such changes will be encountered in vivo as well as in vitro.

The therapeutic agent can be any therapeutic agent compatible with liposome or lipid vehicle delivery. Since the liposomes help to selectively deliver the therapeutic agent, side effects of the agent are typically lower and efficacy is enhanced. Further, the method can be combined with thermally activated liposomes to enhance and control drug delivery at the desired tissue. Such agents can include oligonucleotides, nucleic acids (e.g. for gene therapy), peptides, enzymes, and antibodies. Typically, low molecular weight (e.g. <2500 M.W.) drugs will be used, such as anticancer agents. The therapeutic agent is selected from the group consisting of a compound having a molecular weight of less than 1500 grams per mole and a low permeability to said liposome, and a compound having a molecular weight of less than 1500 grams per mole and lipophilic for said bilayer. Usually, such compounds have an EC50 of less than 1 micromolar for inhibiting proliferation of a cancer cells in vitro.

The invention also provides for methods of drug delivery, drug delivery monitoring, tumor killing, tumor regression, tumor growth monitoring and drug dosing based on delivery in a mammal. The drug delivery method can comprise:
a) administering to a mammal need thereof a composition, comprising:
  i) a paramagnetic chelate with a paramagnetic ion, said paramagnetic chelate is in an amount sufficient to enhance NMR imaging,
  ii) a liposome comprising a bilayer and an interior volume, wherein said liposome is in an amount sufficient to permit delivery of said liposome to a tissue, and said liposome carries said paramagnetic chelate,
  iii) a polyalkylether associated with said liposome, and
  iv) a therapeutic agent in an therapeutic amount, wherein said liposome carries said therapeutic agent, and
b) MNR imaging a tissue of said mammal.

This method is particularly useful in a human suspected of having a proliferation of a cellular mass. It can also be used with other imaging techniques and devices, as described herein. Imaging can begin pre-administration of drug using a similar composition to determine the best liposome size or after injection to follow the biodistribution of the liposomes carrying drugs. Typically, the composition is injected into a vessel of a human. Imaging comprises imaging at least 10 hours post injection of said composition or sooner. The composition can be administered using a device selected from the group consisting of an intravenous syringe injection, a catheter, an intravenous drip and an intraperitoneal syringe injection. A lipid dosage range can be established using known methods and can include a dose of 0.10 to 0.50 millimoles of lipid per kilogram of body weight.

Alternatively, the present invention provides for a method of monitoring drug delivery in a mammal, comprising:
c) administering to a mammal need thereof a composition, comprising:
  i) an imaging agent in an amount sufficient to enhance NMR imaging,
  ii) a liposome comprising a bilayer and an interior volume, wherein said liposome
    1) is in an amount sufficient to permit delivery of said liposome to a tissue, 2) carries said imaging agent, 3) enhances imaging compared to the absence of said imaging agent and 4) selectively distributes said imaging agent to a tumor tissue compared to a non-tumor tissue,
  iii) a polyalkylether associated with said liposome, and
  iv) a therapeutic agent in an therapeutic amount, wherein said liposome carries said therapeutic agent, and
d) imaging a tissue of said mammal, wherein said imaging can image said imaging agent in said tissue.

Specific delivery of liposomes to a target tissue such as a proliferating cell mass, neoplastic tissue, inflammatory tissue, inflamed tissue, and infected tissue can be achieved by selecting a liposome size appropriate for delivering a therapeutic agent to said target tissue. For example, liposomes with a mean diameter of 180 nm may not accumulate in a solid tumor; preferably liposomes with a mean diameter of 140 nm accumulate in the periphery of the same solid tumor, and preferably liposomes with a mean diameter of 110 nm accumulate in the peripheral and central portions of that solid tumor.

In another embodiment of the invention, liposome preparations of different sizes carrying imaging agents can be used to probe capillary permeability and pore size in vivo. This information can be used to determine the optimal particle size of liposomes carrying therapeutic agents for treatment of a particular type of disease in a few experiments (e.g. 2–3). Since tumors are biologically heterogeneous and even the same tumor type may behave differently between different patients, this information can be very useful for tailoring liposome size and for the most advantageous preparation for treatment of a particular type of disease such as cancer or inflammatory tissue.

Specificity of delivery of liposomes to a target tissue may be further enhanced by labelling the liposomes with antibodies (e.g. therapeutic agents) or other tissue markers. Antibody labelling can be used to achieve or enhance intracellular delivery of the therapeutic agent.

Preferably, the imaging is quantitative and amount of said liposome delivered to said tissue can be estimated and the amount of selectively delivered drug calculated. These methods can be combined with methods of monitoring tissue mass to evaluate the therapeutic effectiveness of the drug delivery method and the drug. For instance, determining the volume of the tissue in order to monitor tissue volume, to indicate tissue proliferation, or to monitor a reduction in tissue mass can be accomplished. Such methods may also be used to determine the optimal delivery regime to a particular pathologic tissue in a particular patient.

The invention can be used for a variety of therapeutic agents, including anticancer agents (such as vincristine, vinblastine, dactinomycin, doxorubicin, daunorubicin, cis-platinum, bleomycin, busulfan, carboplatin, chlorambucil, cyclophosphamide, dacarbazine, ifosfamide, lomustine, melphalan, pipobroman, and streptozocin), antifungal agents (such as amphotericin B, fluconazole, flucytosine, griseofulvin, ketoconazole, miconazole, nystatin, terconazole, tioconazole, and sulconazole), antiviral agents (such as acyclovir, amantidine, ganciclovir, ribavirin, vidarabin, and zidovudine), and antiinflammatory and anti-rheumatic agents; see also *The Physician's Desk Reference* 1996 and 1997 for other examles of such agents.

EXAMPLES

General Materials and Methods

Preparation of Sterically Stabilized Liposomes Carrying Gd-Chelates for Magnetic Resonance Imaging Liposomes were composed of egg. phosphatidylcholine, cholesterol, and polyethylene glycol derivatized phosphatidylethanolamine [PEG-PE, i.e. N-(w-methoxypoly (oxyethylene)-α-carbonyl)-1,2-distearyl-3-SH-phosphatidylethanolamine (DSPE)], (molar ratio 3:2:0.3, respectively). Formation of liposomes and encapsulation of Gadolinium-diethylene-triamine-pentaacetic-acid-bis-methylamide (Gd-DTPA-BMA) into sterically stabilized liposomes was performed using the repeated freeze-thaw method followed by extrusion (see Olson, et al. "Preparation of liposomes of defined size distribution by extrusion through polycarbonate membranes" Biochimica et Biophysica Acta, 557, 9–23, (1979)). Extrusion was performed through polycarbonate membranes with pore diameters ranging from 0.1 to 0.05 μm, producing unilamellar liposomes of about 150 mn, 135 nm, or 110 nm in mean diameter, respectively, as determined by dynamic light scattering (Coulter N4 particle size analyser). Non-encapsulated materials was removed using sephadex G-50 gel-exclusion chromatography.

NMR Relaxometry and Magnetic Resonance Imaging

NMR relaxometry and magnetic resonance (MR) imaging were performed using a 2.0 Tesla small bore magnet (Bruker Omega 2.0T System, Bruker Instruments, Inc., Fremont, Calif.) equipped with actively shielded gradients (Accustar™ S-150, Bruker Instruments, Inc., Fremont, Calif.) capable of delivering field gradients up to 20 G/cm along each axis (X, Y and Z).

Example I

Analytic Characterization of GdDTPA-BMA Containing Liposomes in Vitro Using NMR Relaxometry T1 relaxation rates of various liposome suspensions with a mean diameter of 110 nm were determined by standard inversion recovery measurement. The content of GdDTPA-BMA in liposome suspensions was estimated from NMR relaxometry. An inversion recovery NMR spectroscopy pulse sequence was performed in which a nonselective composite inversion pulse (90x-180y-90x) was applied, followed by a gradient spoiler pulse to eliminate residual coherent in-plane magnetization. After a variable delay time (TI), z-magnetization was sampled by a nonselective 90° radiofrequency pulse and the signal was recorded. The inversion recovery signal profile was obtained from at least forty such measurements in which the TI delay was incremented from 20 ms to a value that was at least 3-fold greater than the T1. T1 values were derived from a 3 parameter nonlinear fit of these data to the standard equation describing magnetization recovery following inversion:

$$Mz(TI)/M_\infty = 1 - k\, \exp(TI/T1) \qquad \text{Eq. 1,}$$

in which Mz(TI) is the signal intensity measured at a particular value of TI, $M_\infty$ is the fully relaxed signal intensity, and k has the value of 2.0 if the inversion pulse is exactly 180°. The nonlinear fit optimized values for $M_\infty$, k, and T1. All spectra were acquired under fully relaxed conditions. These measurements produced the following values for different solutions of liposomes with and without GdDTPA-BMA:

Solution A. 110 nm PEG liposomes prepared without GdDTPA-BMA, total lipid=34 mM, was diluted 10 fold in HEPES buffer (0.02 M HEPES, 0.144 M NACl; pH=7.2; 290 mOsm/L). This solution served as a diamagnetic control for intact liposomes.

$T1=2.57$ s

Solution B. 1 part of detergent solution, 1% by weight of octaethyleneglycol dodecyl ether (C12E8) for a final 0.1% detergent concentration, was added to 9 parts of Solution A. This concentration of detergent solubilizes the liposomes. This solution served as diamagnetic control for solubilized liposomes.

$T1=2.67$ s

Solution C. 1 part of 0.5M GdDTPA-BMA was added to 499 parts of solution B. This solution was used to determine the relaxivity of GdDTPA-BMA in solution of solubilized liposome.

$T1=0.225$ s.

Relaxivity=$\Delta R1/[Gd]$=(1/0.225−1/2.67)/1 mM=4.07 $s^{-1}mM^{-1}$

Solution D. 110 nm PEG liposomes, total lipid=33.77 mM, containing 0.25 M GdDTPA-BMA. This solution was diluted 10 fold in HEPES buffer and T1 was measured.

$T1=0.39$ s.

Solution E. 1 part of detergent solution, containing 1% by weight of C12E8, was added to 9 parts of solution D.

$T1=0.325$ s.

Concentration of GdDTPA-BMA was then calculated as ΔR1×dilution factor divided by the relaxivity of GdDTPA-BMA in solubilized liposomes. Thus, (1/0.325−1/2.67)×11= 29.7 $s^{-1}$÷4.07 $s^{-1}mM^{-1}$=7.3 mM GdDTPA-BMA in stock solution, resulting in a [Gd]:[lipid]total ratio of 0.22.

A more useful number is the T1 relaxivity of the solution in terms of liposome concentration rather than [Gd] or [lipid]total. This number can be obtained as follows:

a) Assuming that the concentration of entrapped GdDTPA-BMA is equal to that used in preparing the liposomes i.e. 0.25 M GdDTPA-BMA, then the total volume of entrapped contrast agent equals 0.0073/0.25=0.029; or 2.9% of solution volume is enclosed in liposomes. The number of liposomes in solution is then obtained by dividing the total entrapped volume by the median volume per liposome. The volume enclosed per liposome (using $V=\pi d^3/6$) is ~7×10–16 $cm^3$. Then the number of lipid particles in a 1.0 ml volume of solution is 0.029 ml/ml/7×10–16 ml/liposome 4.2×10$^{13}$ liposomes/ml. In units of molarity this is 6.9×10$^{-8}$ M. Then the relaxivity expressed in terms of concentration of intact liposomes is obtained from:

$(1/0.39-1/2.57) \times$ dilution factor $\sqrt{6.9 \times 10^{-5}}$ mM=3.2×10$^5$ s$^{-1}$ mM$^{-1}$ liposome.

These measurements and calculations allow descriptions of the liposome preparation that would otherwise require substantial tine, effort and specially prepared solutions with radiolabeled tracers. In addition with the T1 relaxivity expressed per unit concentration of liposome allows approximate calculation of quantity of liposome vehicle delivered to target pathology in patients from Signal intensity change observed on MRI images (see Examples 4 and 5) a measurement which is otherwise not currently feasible.

Finally, the difference in T1 relaxation rate observed upon solubilizing the liposomes, a 37% increase in the description above, can be exploited in a very useful way. The invention includes methods to rupture liposomes by externally applied perturbations such as hyperthermia (including therapeutic ultrasound) would be detectable, in principle, because the substantial increased T1 relaxation potency which occurs when entrapped GdDTPA-BMA is liberated by destruction of the liposome structure would be easily observable on MRI imaging.

Example II
Imaging of Neoplastic Tissue Using Gd-DTPA-BMA Containing Liposomes as a Means of Monitoring Delivery of Drugs and Agents Carried by Liposomes to a Target Tissue The diagnostic method of the present invention was used to accurately demonstrate delivery of liposomes to neoplastic tissue in tumor-bearing nude athymic rats, using the osteogenic sarcoma cell line UMR 106 (ATCC CRL 1661). This rat osteogenic sarcoma cell line and the nude athymic rat animal model have been established as accurate models for osteosarcoma in humans (see Witzel and Prescher "An experimental osteosarcoma of the athymic nude rat" Invasion Metastasis, 11, 110–115, (1991), Witzel, et al. "Osteosarcoma of the nude rat: a model for experimental magnetic resonance imaging studies of bone tumors" Invest Radiol, 27, 205–210, (1992)).

Samples of the rat osteogenic sarcoma cell line (UMR 106) were implanted subcutaneously into the left hind leg of 4 nude athymic rats (Harlan Sprague Dawley, Inc., San Diego, Calif.). Specifically, an approximately 2 mm large fragment of viable tumor was excised from a tumor-bearing rat, and implanted directly into the left hind leg after subcutaneous and fascial incision. Alternatively, a solution containing 2 million tumor cells obtained from cell culture and 2 ml of normal saline was injected subcutaneously through a 16 G needle. The tumors were allowed to grow for 10–12 days until a palpable mass measuring 1–3 cm in diameter was present.

Magnetic Resonance Imaging

Prior to magnetic resonance imaging each animal was anesthetized by intraperitoneal injection of a mixture of Ketamine and Xylazine. Each animal was placed supine in a plastic holder, with the legs extended and lightly secured, and inserted into a homebuilt "birdcage" imaging coil (5.6 cm inner diameter) such that the tumors were in the center of the coil. The preparation was then inserted into the magnet with the center of the imaging coil aligned with the center of the imaging gradients. A 5 mm NMR sample tube filled with Gd-DPTA-doped water (gadolinium-diethylene triamine pentaacetic acid, a contrast agent, sold as Magnevist™, Berlex, Cedar Hills, N.J.) was placed alongside each animal to provide a T1-relaxation reference. The Gd-DPTA was used at a concentration sufficient to give a $T_1$ relaxation time of the phantom of approximately 450 msec.

Magnetic resonance imaging was performed on a 2.0 Tesla small bore magnet (Bruker Omega 2.0T System, Bruker Instruments, Inc., Fremont, Calif.) equipped with actively shielded gradients (Accustar™ S-150, Bruker Instruments, Inc., Fremont, Calif.) capable of delivering field gradients up to 20 G/cm along each axis (X, Y and Z). The imaging sequences used were as follows: $T_1$-weighted spin-echo and, in 2 animals, $T_2$-weighted double-echo spin-echo images to achieve improved tumor tissue characterization.

All images were obtained as multislice acquisitions (contiguous slices=8) for complete coverage of the tumor and surrounding non-tumorous tissues. In-plane dimensions of each image were 4.0×4.0 cm defined by a raw data matrix of 256×128 points interpolated to 256×256 pixels in reconstructed images. The T1-weighted images were obtained with TR and TE set to 400 and 12 msec, respectively. $T_2$-weighted images were obtained with TR set to 2500 msec and TE set to 40 and 80 msec in a double echo acquisition. After completion of precontrast imaging, 110 nm liposomes carrying Gd-DTPA-BMA were injected intravenously via the rat's tail vein using a dose of 0.05 mmol/kg body weight Gd-DTPA-BMA. T1-weighted images were repeated 5 min after injection of the liposomal contrast agent. Additionally, animals were re-imaged at 24, 48, 72, and 96 hours after injection. After 96 hours, once the last imaging experiment had been completed, the animals were sacrificed and the tumor bearing leg was excised. Tumor tissue was fixed in formaldehyde for future histologic analysis. Signal intensity of the tumor periphery and the tumor center were measured on the MR images obtained at the different time intervals. Signal intensity of tumor periphery and tumor center were then normalized to that of normal muscle measured in each animal for each time point.

MR images obtained 5 minutes after injection of Gd-labeled liposomes demonstrated vascular enhancement, but only minimal enhancement of the tumor tissue. After 24 hours, definite signal enhancement was observed in the tumor tissue in all four animals confirming accumulation of the liposome compound in the neoplastic tissue. This enhancement can, in part, be attributed to abnormal capillary permeability resulting in leakage of liposomes into the tumor tissue. Normal tissues demonstrated no enhancement.

Enhancement of tumor tissue reached a maximum at 24 hours after injection. At 48, 72 and 96 fours, signal intensity of the enhanced tumor tissue decreased progressively (FIG. 1). The decrease in signal intensity at 48, 72 and 96 hours is thought to be secondary to degradation of the liposome membranes with resultant release of free Gd-DTPA-BMA. Free Gd-DTPA-BMA was probably cleared through the kidneys.

Since unencapsulated, free Gd-DTPA and Gd-DTPA-BMA have a biologic half-life of approximately 30 min see Rocklage and Watson "Chelates of gadolinium and dysprosium as contrast agents for MR imaging" JMRI, 3, 167–178, (1993, Oksendal and Hals "Biodistribution and toxicity of MR imaging contrast media" JMRI, 3, 157–165, (1933), it is evident that the enhancement seen in the periphery and in the center of the tumor at 24 hours and later confirms delivery of the liposomes with encapsulated Gd-DTPA-BMA to the tumor. Thus, liposomes with prolonged circulation times such as the formulation used in this example containing polyethylene-glycol that carry MR contrast media can be used to monitor delivery of liposome based drugs to a target tissue such as a tumor non-invasively in-vivo.

One modification of the present example is to co-inject liposomes containing Gd-DTPA-BMA or other paramagnetic contrast media with liposomes containing therapeutic agents. If both liposome formulations are of identical size and chemical composition, biodistribution of both liposome populations will be identical and delivery of the liposomes to the target tissue can be monitored with MR imaging noninvasively in-vivo.

Another modification of the present example is to encapsulate both Gd-DTPA-BMA or other MR contrast media and therapeutic agents into the same liposomes. In this case, MR imaging can also be used to monitor delivery of the liposomes to the target tissue non-invasively in-vivo.

Tumors continued to grow during the 5-day experiment. The approximate doubling time of the Osteogenic sarcoma was 2–3 days in these immunedeficient, nude athymic animals. 72 and 96 hours after injection, several tumors showed areas with low signal intensity on T1-weighting without any evidence of contrast enhancement adjacent to areas with enhancement noted on the 24 and 48 hours study. The unenhanced areas seen at 72 and 96 hours are thought to represent viable tumor, while the unenhanced regions mark new tumor tissue that has formed after the blood pool concentration of the liposomal contrast agent has decreased. In this case, liposomal contrast agents can be used to monitor tumor growth in rapidly growing tumors, since new, viable tumor may not show significant enhancement.

Example III

Comparison of Different Liposome Sizes in Waging Neoplastic and Other Tissues

The same as example 2, except that liposomes with a mean diameter of 135 nm and 150 nm were separately injected. Four animals were injected intravenously via the rat's tail vein with liposomes with a mean diameter of 135 nm carrying Gd-DTPA-BMA using a dose of 0.05 mmol/kg body weight Gd-DTPA-BMA. One animal was injected intravenously via the rat's tail vein with liposomes with a mean diameter of 150 nm carrying Gd-DTPA-BMA using a dose of 0.05 mmol/kg body weight Gd-DTPA-BMA. Signal intensity of the tumor periphery and the tumor center were measured on the MR images obtained at the different time intervals in. all animals. Signal intensity of tumor periphery and tumor center were then normalized to that of normal muscle measured in each animal for each time point. Normalized signal intensities of tumor periphery and tumor center measured at each time interval were then compared between 150 nm and 135 nm liposomes as well as 110 nm liposomes described in Example II.

TABLE 1 shows the normalized mean MR signal intensity of tumor periphery and tumor center for 150 nm, 135 nm, and 110 nm liposomes imaged at various time intervals before and after intravenous injection.

| Tumor Region | Particle Size | Pre-injection | 5 min after injection | 24 hours | 48 hours | 72 hours | 96 hours |
|---|---|---|---|---|---|---|---|
| Tumor Periphery | 150 | 1.0640 | 1.1219 | 1.0825 | | | |
| | 135 | 1.0206 (±0.0059) | 1.0435 (±0.0899) | 1.4475 (±0.0900) | 1.3012 (±0.0144) | 1.1530 (±0.0854) | 1.0665 (N/A) |
| | 110 | 1.1162 (±0.0231) | 1.2873 (±0.1967) | 1.7330 (±0.2886) | 1.4689 (±0.2073) | 1.1668 (±0.0644) | 1.1083 (±0.0363) |
| Tumor Center | 150 | 1.018628 | 1.050222 | 1.050129 | | | |
| | 135 | 0.9964 (±0.0614) | 1.0455 (±0.0608) | 1.1644 (±0.0163) | 1.1169 (±0.0226) | 1.0343 (±0.0541) | 1.0612 (N/A) |
| | 110 | 1.0920 (±0.0413) | 1.1473 (±0.0931) | 1.4643 (±0.2111) | 1.2402 (±0.0213) | 1.0764 (±0.0325) | 1.0278 (±0.0483) |

Value in parentheses: ±1 standard deviation
N/A: not available (only one animal imaged at 96 hours in this group; standard deviation could not be calculated).

Twenty-four hours after injection, 110 nm liposomes demonstrated no statistically significant difference in signal density between tumor periphery and tumor center (p<0.07, paired t-test). Similar to 110 nm liposomes, animals that had been injected with the 135 nm liposomes demonstrated also maximum tumor enhancement after 24 hours. However, with the 135 nm liposomes, the enhancement observed in the tumor periphery was statistically significantly higher than that seen in the tumor center (p<0.005). Overall, unlike 110 nm liposomes, enhancement in the center of the tumor was minimal with 135 nm particles. 150 nm liposomes demonstrated intravascular enhancement. Minimal enhancement of neoplastic tissue was observed in the tumor periphery only 5 min after injection. This enhancement was most likely the result of fine neovascularity in the periphery of the tumor. However, 24 hours after injection neither the tumor periphery nor the tumor center demonstrated any detectable enhancement for the 150 nm liposomes. This is most likely the result of the particle size which was probably too large to pass through the capillary pores of the tumor.

These results indicate that the size of the liposomes is of critical importance in order to achieve adequate enhancement of neoplastic and other tissues with abnormal capillary permeability. Liposomal MR contrast agents can be used to probe capillary permeability and pore size in vivo. This information scan be used to determine the optimal particle size of liposomes carrying therapeutic agents for treatment of a particular type of disease. Since tumors are biologically extremely heterogeneous and even the same tumor type may behave differently between different patients, this information can be very useful for selecting the most advantageous liposome size and preparation for treatment of a particular type of disease such as cancer.

Example IV
Co-Injection of Liposomes Containing Gd-DTPA-BMA and Liposomes Containing Colloidal Gold in an Animal Model of Rat Osteogenic Sarcoma as a Means of Monitoring Delivery of Drugs and Agents Carried by Liposomes to a Target Tissue The same protocol was used as in Example 2, except that liposomes with a mean diameter of 110 nm containing Gd-DTPA-BMA were co-injected with 110nm liposomes containing colloidal gold. Injection was performed intravenously via the rat's tail vein. Initially, liposomes containing Gd-DTPA-BMA were injected. Immediately after completion of injection with liposomes containing Gd-DTPA-BMA, liposomes containing colloidal gold were injected. Chemical composition of liposomes containing colloidal gold was identical to that of liposomes containing Gd-DTPA-BMA. MR imaging was performed prior to injection and 5 min and 24 hours after injection. Tumor signal intensity was measured on the MR images for all time intervals and normalized to that of muscle. Normalized mean signal intensity of the tumor prior to injection, 5 min after injection, and 24 hours after injection was 1.09, 1.31, and 1.65. Thus, the signal intensity of the tumor increased 51% at 24 hours after injection which is comparable to the enhancement observed in Example II.

These data indicate that co-injection of liposomes carrying MR contrast agents and liposomes carrying therapeutic and other agents does not result in significantly decreased uptake of liposomes in the tumor due to competition between both liposome populations. Liposomes carrying MR contrast agents can be co-injected with liposomes carrying therapeutic and other agents thereby affording non-invasive monitoring of delivery of such agents to the target tissue.

Example V
Noninvasive Quantification of Amount of Liposomes Delivered to Neoplastic Tissue As a demonstration of the potential utility of using MR imaging of Gd-labelled liposomes to monitor delivery of encapsulated drug to a target pathologic lesion the following simple calculation was performed. At 24 hrs post injection of Gd-DTPA-BMA containing liposomes, dose=0.05 mmol GdDTPA-BMA/kg body weight, the tumor signal intensity was maximally enhanced. The enhancement within each tumor was somewhat heterogeneous putatively due to a heterogeneous accumulation of GdDTPA-BMA containing liposomes within the tumor. Signal intensity was greatest at the periphery of the tumor (typically 60 to 80% enhancement over preinjection values) and less in the central portions of the tumor (typically 25–60% enhancement over preinjection values) (see Example II). The magnitude of enhancement can be used to approximate the number of liposome particles carrying Gd-DTPA-BMA that accumulated within various regions of the tumor. Using a nominal value for tumor T1 of 1.1 s prior to administration of contrast material and a TR value of 0.3 s, the signal intensity would be saturated by a factor (SF), defined as SF=(SIrelaxed−SI)/SIrelaxed=exp(−TR/T1), of 0.76. Shortening of T1 caused by addition of Gd-DTPA-BMA-containing liposomes decreases the saturation factor and thereby increases the observed signal intensity. From the decrease in saturation factor is it possible to calculate the change in T1 relaxation rate ($\Delta R1$) and thereby to estimate the quantity of liposomes present in the respective pixels of the image. The change in saturation factor can be estimated by a number of different methods, in this case we use change in relative signals of tumor and adjacent muscle tissue.

The relationship between change in saturation factor and $\Delta R1$ is shown below:

$$SFpre/SFpost = \exp(-TR*R1pre)/\exp(-TR*R1post) = \exp(TR(R1post - R1pre))$$

$$\ln[SFpre/SFpost] = TR*\Delta R1$$

$$\Delta R1 = \ln[SFpre/SFpost]*1/TR$$

Where SFpost is obtained from SFpre and the measured relative signal intensity (SI) change as shown below:

$$SFpost = 1.0 - (SIpost/SIpre(1.0 - SFpre))$$

Thus for a relative signal increase of 30% caused by addition of GdDTPA-BMA-liposomes on MRI images obtained with TR=0.3 s and SFpre of tumor=0.76, the $\Delta R1$ is 0.33 $s^{-1}$. Dividing this number by the relaxivity of liposomes obtained in Example (1), $3.2 \times 10^8$ $s^{-1}$ $M^{-1}$, yields the liposome concentration of 1.03 nM in the tumor. This is equivalent to $6.2 \times 10^{11}$ liposomes/cc of tumor or 0.43 $\mu L$ liposome interior/cc of tumor.

Thus, from this example calculation it is shown how one can approximate the relative volume of liposome contents (i.e. drug) that accumulates within the tumor following administration of liposome. It is presumed that drug-containing liposomes would be (a) coinjected with Gd-containing liposomes, in which case the dosage of drug delivered to the tumor would be the quantity of Gd-liposome measured multiplied by the ratio of doses (drug containing liposomes/Gd-containing liposomes) in the coinjected solutions, (b) prepared with both GdDTPA-BMA and drug co-dissolved in the same liposomes, or (c) drug is enclosed in liposomes with surface-attached Gd-chelate. In all cases, it is possible to approximate the quantity of drug delivered to the target lesion (tumor) from measured MR signal enhancement.

Example VI
Mapping of Delivery of Liposomes into Tumor

The calculations employed in the previous example (Example V) can be used to compute an image whose pixel values are scaled to represent number of liposome particles accumulated within the pixel, or a related quantity such as volume or mass of drug enclosed within the liposome. This manipulation requires some simplifying assumptions because the pre- and postcontrast images would be obtained with a time separation of 24 hours and thus could not be done within a single imaging session. The postcontrast maps would be based upon postcontrast signal intensities of each pixel and on intensity of anatomic features observable on precontrast images, in the event that the tumor contains multiple identifiable regions on precontrast T1-weighted images.

Example VII
Treatment and Monitoring of a Tumor

The same protocol is used as in Example 2, except that liposomes with a mean diameter of 110 nm are made containing Gd-DTPA-BMA (or mean diameter of 70 nanometers), doxorubicin and bleomycin. Liposomes are injected i.v. at baseline. Injections are repeated at one day and 5 days. Repeat injections can also start 48 hours or less after injection and tumor mass monitored before and after injection of therapeutic imaging liposomes. Injection is performed intravenously via the rat's tail vein. MR imaging is performed prior to injection and 5 min and 24 hours, 5 days and 10 days after injection. Tumor signal intensity is measured on the MR images for all time intervals and normalized to that of muscle.

Such experiments can indicate that injection of therapeutic-imaging liposomes carrying MR contrast agents and therapeutic agents reduces tumor growth, inhibits pathologic cell proliferation and in some instances promotes tumor regression (where the tumor size actually decreased as opposed abatement of tumor growth post treatment). Such treatments are expected to work more effectively in mammals with intact immune systems or immuno-boosted systems (co-treatment with immunoboosting agents).

Publications

The patent documents and the articles cited herein are herein incorporated by reference to the same extent as if each publication had been individually incorporated by reference.

Articles

Brasch "Rationale and applications for macromolecular Gd-based contrast agents" Magn Res Med, 22, 282–287, (1991)

Gaber, et al. "Thermosensitive sterically stabilized liposomes: formulation and in vitro studies on mechanism of doxorubicin release by bovine serum and human plasma" Pharmaceutical Research, 12, 1407–1416, (1995)

Harding, et al. "Immunogenicity and pharmacokinetic attributes of poly(ethylene glycol)-grafted immunoliposomes" Biochim Biophys Acta, 1327, 2, 181–192, (1997)

Huang, et al. "Liposomes and hyperthermia in mice: increased tumor uptake and therapeutic efficacy of doxorubicin in sterically stabilized liposomes" Cancer Research, 54, 2186 . 2191, (1994)

Kirpotin, et al. "Sterically stabilized anti-HER2 immunoliposomes: design and targeting to human breast cancer cells in vitro" Biochemistry 36, 1, 66–75, (1997)

Lang, et al. "Targeted Gadolinium-labeled liposomes: a novel approach to monitor chemotherapy in osteogenic sarcoma" Society for Pediatric Radiology, (1997)

Lasic and Papahadjopoulos "Liposomes revisited" Science, 267, 1275–1276, (1995)

Oksendal and Hals "Biodistribution and toxicity of MR imaging contrast media" JMRI, 3, 157–165, (1933)

Olson, et al. "Preparation of liposomes of defined size distribution by extrusion through polycarbonate membranes" Biochimica et Biophysica Acta, 557, 9–23, (1979)

Papahadjopoulos, et al. "Sterically stabilized liposomes: improvements in pharmacokinetics and antitumor therapeutic efficacy" Proc. Natl. Acad. Sci, USA, 88, 11460–11464, (1991)

Papahadjopoulos and Gabizon "Sterically stabilized (stealth) liposomes: pharmacological properties and drug carrying potential in cancer" Liposomes as tools in basic research and industry, 177–223, (1995)

Park, et al. "Anti-HER2 immunoliposomes for targeted therapy of human tumors" Cancer Letters 118, 2, 153–160, (1997)

Rocklage and Watson "Chelates of gadolinium and dysprosium as contrast agents for MR imaging" MRI, 3, 167–178, (1993)

Seltzer, et al. "Contrast material-carrying liposomes: biodistribution, clearance, and imaging characteristics" Radiology, 194, 775–781, (1995)

Storrs, et al. "Paramagnetic polymerized liposomes as new recirculating MR contrast agents" JMRI, 5(6), 719–724, (1995)

Tilcock, et al. "Liposomal Gd-DTPA: preparation and characterization of relaxivity" Radiology, 171, 77–80, (1989)

Tilcock, et al. "Nuclear magnetic relaxation dispersion and 31P NMR studies of the effect of covalent modification of membrane surfaces with polyethyleneglycol" Biochim Biophys Acta, 193, 1110, (1992)

Tilcock "Imaging tools: liposomal agents for nuclear medicine, computed tomography, magnetic resonance, and ultrasound" Liposomes as tools in basic research and industry, 225–242, (1995)

Trubetskoy and Torchilin "Controlled delivery of imaging agents to lymph nodes: membranotropic polychelating agent for incorporation into liposomes" Proc. Intern. Symp. Control. Rel. Bioact. Mater., 20, 380, (1993)

Trubetskoy, et al. "Controlled delivery of Gd-containing liposomes to lymph nodes: surface modification may enhance MRI contrast properties" Magn Res Imaging, 13, (1995)

Unger, et al. "Hepatic metastases: liposomal Gd-DTPA-enhanced MR imaging" Radiology, 171, 81–85, (1989)

Unger, et al. "Gadolinium-DTPA liposomes a potential MRI contrast agent: work in progress" Invest Radiol, 23, 928–932, (1988)

Witzel and Prescher "An experimental osteosarcoma of the athymic nude rat" Invasion Metastasis, 11, 110–115, (1991)

Witzel, et al. "Osteosarcoma of the nude rat: a model for experimental magnetic resonance imaging studies of bone tumors" Invest Radiol, 27, 205–210, (1992)

Woodle "67Gallium-labeled liposomes with prolonged circulation: preparation and potential as nuclear imaging agents" Nucl Med Biol, 20, 149–155, (1993)

Patents

U.S. Pat. No. 3,932,657 Jan. 13, 1976 "Liposome encapsulation of chelating agents" Rahman, Y. E.

U.S. Pat. No. 4,728,575 Mar. 1, 1988 "Contrast agents for NMR imaging" Gamble, R. C. and Schmidt, P. G.

U.S. Pat. No. 4,873,088 Oct. 10, 1989 "Liposome drug delivery method and composition" Mayhew, E., Ehrke, M. J., Mace, K., Szoka, F. and Olson, F. C.

U.S. Pat. No. 4,985,233 "A diagnostic agent containing a non-radioactive paramagnetic metal species in a macromolecular carrier" Klaveness, J., facobsen, T. and Lindberg, B. J.

U.S. Pat. No. 5,013,556 May 7, 1991 "Liposomes with enhanced circulation time" Woodle, M. C., Martin, F. J., Yau-Young, A. and Redemann, C. T.

U.S. Pat. No. 5,019,369 May 28, 1991 "Method of targeting tumors in humans" Presant, C. A. and Proffitt, R. T.

U.S. Pat. No. 5,387,410 Feb. 7, 1995 "Method for enhancing magnetic resonance with compositions containing paramagnetic elements carried by liposomes" Bosworth, M. E. and Hopkins, R. M.

U.S. Pat. No. 5,393,530 Feb. 28, 1995 "Method for making liposomes of enhanced entrapping capacity toward foreign substances to be encapsulated" Schneider, M., Tournier, H., Hyacinthe, R., Guillot, C. and Lamy, B.

U.S. Pat. No. 5,407,660 Apr. 18, 1995 "Diagnostic liposomal compositions for enhancing NMR imaging" Bosworth, M. E. and Hopkins, R. M.

U.S. Pat. No. 5,545,395 Aug. 13, 1996 "Method of imaging using encapsulated magnetite particles" Tournier, H., Hyacinthe, R. and Schneider, M.

U.S. Pat. No. 5,512,294 Apr. 30, 1996 "Targeted polymerized liposome contrast agents" Li, K., Bednarski, M. D., Storrs, R. W., Li, H. Y., Trooper, F. D., Song, C. K. H., Sipkins, D. A. and Kuniyoshi, J. K.

U.S. Pat. No. 5,527,528 Jun. 18, 1996 "Solid-tumor treatment method" Allen, T. M. and Martin, F. J.

U.S. Pat. No. 5,593,688 Jan. 14, 1997 "Liposomal targeting of ischemic tissue" Baldeschwieler, J. D.

We claim:

1. A composition for NMR imaging during drug delivery, comprising:
   a) a paramagnetic chelate with a paramagnetic ion and in amount sufficient to enhance NMR imaging,
   b) a liposome comprising a bilayer and an interior volume and in an amount sufficient to permit delivery of said liposome to a tissue, wherein said liposome carries said paramagnetic chelate,
   c) a polyalkylether associated with said liposome, and
   d) a therapeutic agent in a therapeutic amount, wherein liposome carries said therapeutic agent.

2. The composition of claim 1, wherein said paramagnetic chelate is selected from the group consisting of BOTPA, EHPG, DPDP, DTPA, DOA3 and HBED.

3. The composition of claim 1, wherein said polyalkylether is poly(ethylene glycol).

4. The composition of claim 3 wherein said liposome has an average size distribution selected from the group consisting of 85, 110, 135, and 150 nanometers in diameter.

5. The composition of claim 4, wherein said liposome comprises a molecule selected from the group consisting of phosphatidyl ethanolamine, phosphatidyl choline, dipalmitoyl phosphatidic acid, cholesterol and alpha-tocopherol.

6. The composition of claim 5, wherein said poly(ethylene glycol) is present in the amount 1 to 25 mole percent of total lipid content.

7. The composition of claim 6, wherein said interior volume has a pH of 6.5 to 7.5.

8. The composition of claim 6, wherein said tissue is a solid tumor in a non-reticuloendothelial organ.

9. The composition of claim 3, wherein said therapeutic agent is selected from the group consisting of an oligonucleotide, nucleic acid, peptide, and antibody.

10. The composition of claim 3, wherein said therapeutic agent is selected from the group consisting of a compound having a molecular weight of less than 1500 grams per mole and a low permeability to said liposome, and a compound having a molecular weight of less than 1500 grams per mole and lipophilic for said bilayer.

11. The composition of claim 10, wherein said compound has EC50 of less than 1 micromolar for inhibiting proliferation of a cancer cell in vitro and said composition is contained in a syringe or catheter.

12. The composition of claim 3, wherein said compound is selected from the group consisting of anticancer agents, chemotherapeutic agents, antiinflammatory agents, antiinfectious agents, gene therapy agents, antisense oligonucleotides, ribozymes, and antiviral agents.

13. A method of drug delivery in a mammal, comprising:
   a) administering to a mammal in need thereof a composition, comprising:
      i) a paramagnetic chelate with a paramagnetic ion and in amount sufficient to enhance NMR imaging,
      ii) a liposome comprising a bilayer and an interior volume and in an amount sufficient to permit delivery of said liposome to a tissue, wherein said liposome carries said paramagnetic chelate,
      iii) a polyalkylether associated with said liposome, and
      iv) a therapeutic agent in a therapeutic amount, wherein said liposome carries said therapeutic agent, whereby drug delivery is achieved.

14. The method of claim 13, wherein said mammal is a human suspected of having a proliferation of a cellular mass.

15. The method of claim 14, wherein said polyalkylether is poly(ethylene glycol).

16. The method of claim 14, wherein said composition is administered using a device selected from the group consisting of a intravenous syringe injection, a catheter, an intravenous drip and an intraperitoneal syringe injection.

17. The method of claim 14, wherein said composition is administered at a dose of 0.05 to 2 millimole of lipid per kilogram of body weight.

18. A method of monitoring drug delivery in a mammal, comprising:
   a) administering to a mammal need thereof a composition, comprising:
      i) an imaging agent and in amount sufficient to enhance NMR imaging,
      ii) a liposome comprising a bilayer and an interior volume and in an amount sufficient to permit delivery of said liposome to a tissue, wherein said liposome carries said imaging agent and said liposome enhances imaging compared to the absence of said imaging agent and said liposome selectively distributes said imaging agent to a tumor tissue compared to a non-tumor tissue,
      iii) a polyalkylether associated with said liposome, and
      iv) a therapeutic agent in an therapeutic amount, wherein said liposome carries said therapeutic agent, and
   b) imaging a tissue of said mammal, wherein drug delivery can be monitored.

19. The method of claim 18, wherein said imaging is quantitative and amount of said liposome delivered to said tissue can be calculated and optionally determining a volume of said tissue to monitor as an indication of tissue proliferation or a reduction in tissue mass.

20. The method of claim 18, wherein said liposome further comprises a tissue specific antibody.

21. The method of claim 18, wherein said imaging comprises imaging at a time selected from the group consisting of at least 10 hours post injection, at least 24 hours post injection, at least 48 hours post injection, at least 72 hours post injection, and at least 96 hours post injection.

* * * * *